United States Patent [19]

Cowden et al.

[11] 4,126,130
[45] Nov. 21, 1978

[54] WOUND PROTECTIVE DEVICE

[75] Inventors: Ernest A. Cowden, Kansas City; Leo E. Lauber, Eudora, both of Kans.

[73] Assignee: The Clear Corporation, Eudora, Kans.

[21] Appl. No.: 787,834

[22] Filed: Apr. 15, 1977

[51] Int. Cl.$^2$ .............................................. A61F 5/04
[52] U.S. Cl. .................................... 128/91 R; 128/156
[58] Field of Search .................. 128/91 R, 90, 89 R, 128/87 R, 155, 156

[56] References Cited

U.S. PATENT DOCUMENTS

| | | | |
|---|---|---|---|
| 2,692,596 | 10/1954 | Marconnet | 128/91 R |
| 3,323,519 | 6/1967 | Schramm | 128/91 R |
| 3,923,049 | 12/1975 | Lauber et al. | 128/91 R |

FOREIGN PATENT DOCUMENTS

| | | | |
|---|---|---|---|
| 1,004,773 | 3/1957 | Fed. Rep. of Germany | 128/90 |
| 1,098,164 | 1/1961 | Fed. Rep. of Germany | 128/91 R |
| 1,491,190 | 3/1969 | Fed. Rep. of Germany | 128/91 R |

Primary Examiner—John D. Yasko
Attorney, Agent, or Firm—Lowe, Kokjer, Kircher, Wharton & Bowman

[57] ABSTRACT

A protective device for an injured portion of the body is the subject of the present invention. An adhesive strip is provided with a pocket into which is placed a dry plaster material that may be activated upon submersion in water to present a hardenable material which may be conformed to the configuration of an injured portion of the body. The dry plaster material is in the form of one or more plaster splints comprising a loosely woven gauze cloth impregnated with the dry plaster ingredients. A sterile gauze pad covers the dry plaster material so as to preclude direct contact between the plaster and the injured portion of the body.

5 Claims, 5 Drawing Figures

WOUND PROTECTIVE DEVICE

This invention relates generally to the field of protective bandages and, more particularly, to a wound protective device for forming a substantially rigid shield over an injured portion of the body.

Preformed adhesive bandages have become a popular medical aid, particularly in first aid treatment. Preformed bandages normally utilize an adhesive strip having secured to it a sterile gauze pad which protects the wound or other injury. Bandages of this general type are widely sold in the United States under the trademark "BAND-AID" by the Johnson & Johnson Company.

It is also known in the art to construct an immobilizing cast from a casting blank formed from a number of plaster splints that are enclosed by some form of water absorptive material. This technique is shown in our prior U.S. Pat. Nos. 3,900,024 issued Aug. 19, 1975 and 3,923,049 issued Dec. 2, 1975.

A major shortcoming of preformed bandages of the type above described is their inability to offer any form of semi-rigid protection over the injured portion of the body. Thus, a wound or bruise which is in an area where it is difficult to avoid contact with other objects is often re-injured even though covered with a bandage. The problem is also not solved by the casts of the type shown in the above referenced patents. These casts are intended to provide either immobilization or rigid support to an area of the body but are not practical for use on small injuries that are normally attended by an individual without the benefit of professional knowledge or assistance.

It is, therefore, a primary object of the present invention to provide a wound protective device in the form of a ready-made bandage having an adhesive section for securing it to the body and a section containing a hardenable material for forming a substantially rigid protector over the injured portion.

Another object of the invention is to provide a wound protective device of the type described in the foregoing object which may be manufactured in ready-made form in any one of a variety of sizes and configurations adaptable for different areas of the body.

It is also an important objective of the invention to provide a wound protective device of the type described in the foregoing objects which may be applied by an individual without specialized training or professional assistance.

A very important object of the invention is to provide a wound protective device which will form a substantially rigid shield over an injured portion of the body to prevent re-injury if the particular portion comes into contact with other rigid articles.

Other objects of the invention will be made clear or become apparent from the following description and claims, when read in light of the accompanying drawing, wherein:

Figure 1:
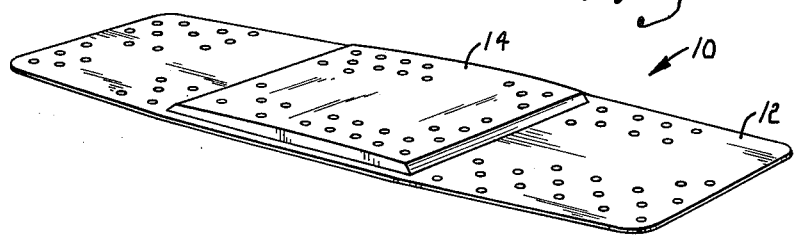
FIG. 1 is a perspective view of the protective device of the present invention.
Figure 2:
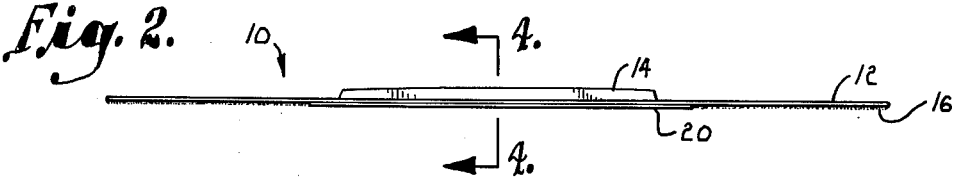
FIG. 2 is a side elevational view of the device shown in FIG. 1.

Referring initially to FIG. 1, the wound protective device of the present invention is designated generally by the numeral 10. Device 10 comprises an elongated perforated plastic strip 12 having a central pocket section 14 and a layer of adhesive 16 on one side thereof.

Figure 3:
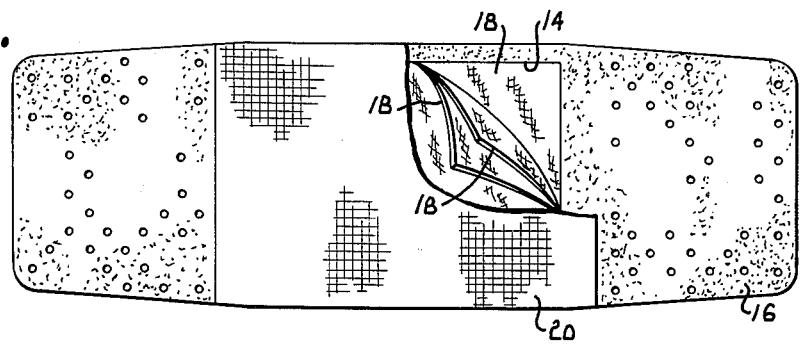
FIG. 3 is a top plan view with portions broken away and folded back of the device shown in FIGS. 1 and 2.
Figure 4:
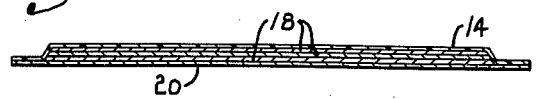
FIG. 4 is a vertical cross-sectional view taken along line 4—4 of FIG. 2.

Disposed within pocket section 14 are a plurality of plaster splints 18 (FIG. 4). As best illustrated in FIG. 3, each of the plaster splints 18 comprises a sheet of loosely woven fabric material that is impregnated with a cementious material such as plaster of paris. The number of splints 18 employed may vary, depending upon the size of the bandage and the degree of rigidity desired. Splints 18 are held within pocket section 14 by a gauze strip 20 that is adhesively secured to plastic strip 12. Strip 20 also provides a sterile surface for contacting an open wound and prevents direct contact between the plaster and the injured portion of the body.

Figure 5:
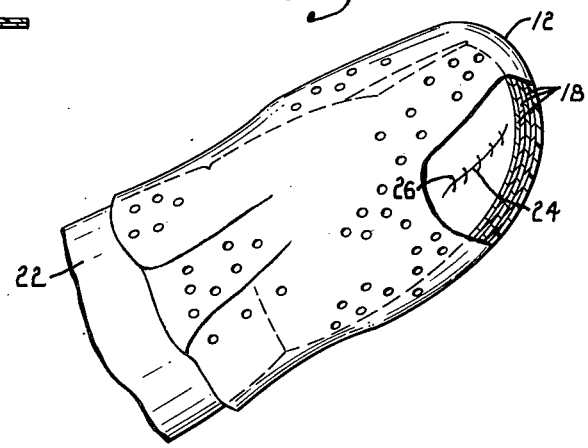
FIG. 5 is an elevational view of the wound protective device conformed to the finger portion of the body to provide a protective shield over a wound area.

In FIG. 5, a finger 22 is shown with a laceration 24 that has been closed with stitches 26. Manifestly, the wound is in a location where it is subject to repeated injury if it is necessary for the individual to use the finger in any manner whatsoever. The bandage device 10 of the present invention is used to form a substantially rigid protective shield over the injury. Device 10 is first placed in contact with sufficient water to activate the plaster of paris and cause the splints 18 to become an amalgamation of moldable material that may readily be shaped to conform to the configuration of finger 22. Once the desired shape is obtained, the bandage device 10 may either be immediately adhesively secured or, if desired, removed until the plaster has hardened to form the substantially rigid shield and then subsequently secured.

The result is a wound protective bandage meeting all of the objects of the present invention which may be readily and economically manufactured. It will be appreciated that it may be desirable to make the protective shield somewhat loosely fitting so as to accommodate the passage of air beneath the shield and into the wound area if the latter is a laceration of the skin. It will also be appreciated, however, that the device of the present invention is not limited to usages of the type where bandages have heretofore commonly been employed but will find great utility in protecting bruises, blisters, broken nails and other injuries that would not normally benefit from a conventional bandage.

Having thus described the invention, we claim:

1. A device for forming a rigid protector over an injured portion of the body, said device comprising:
   a plastic adhesive strip adapted to be secured to body;
   a layer of dry plaster material coupled with said strip, said dry plaster material being adapted to be activated upon contact with water to present a hardenable material which may be conformed to the configuration of the injured portion of the body; and
   means for covering the plaster material to preclude contact between the plaster and said injured portion.

2. A device as set forth in claim 1, wherein is included a carrier sheet having said plaster material impregnated therein.

3. A device as set forth in claim 2, wherein said means for covering the plaster material comprises a gauze pad coupled with said adhesive strip.

4. A device as set forth in claim 3, wherein said adhesive strip extends substantially equidistant in opposite directions from said layer of plaster material.

5. A device as set forth in claim 2, wherein is included a plurality of said carrier sheets impregnated with said plaster material.

* * * * *